United States Patent [19]
Chelvayohan et al.

[11] Patent Number: 6,067,840
[45] Date of Patent: May 30, 2000

[54] METHOD AND APPARATUS FOR INFRARED SENSING OF GAS

[75] Inventors: Mahesan Chelvayohan; Adam J. Ahne, both of Lexington, Ky.

[73] Assignee: Texas Instruments Incorporated, Dallas, Tex.

[21] Appl. No.: 09/088,138

[22] Filed: Jun. 1, 1998

Related U.S. Application Data

[60] Provisional application No. 60/054,671, Aug. 4, 1997.

[51] Int. Cl.⁷ ................................... G01N 21/61
[52] U.S. Cl. ...................... 73/23.2; 73/24.02; 73/31.05; 250/343
[58] Field of Search .................... 73/23.2, 24.02, 73/31.01, 31.02, 31.03, 31.05; 250/343

[56] References Cited

U.S. PATENT DOCUMENTS

| | | | |
|---|---|---|---|
| 4,412,445 | 11/1983 | Spellicy | 73/24.02 |
| 4,899,053 | 2/1990 | Lai | 250/343 |
| 5,163,332 | 11/1992 | Wong . | |
| 5,384,640 | 1/1995 | Wong | 73/31.05 X |
| 5,696,379 | 12/1997 | Stock | 250/343 |

FOREIGN PATENT DOCUMENTS

| | | | |
|---|---|---|---|
| 0709659 | 5/1996 | European Pat. Off. . | |
| 3512284 | 6/1986 | Germany . | |
| 195 20 488 | 9/1996 | Germany . | |
| 62-126329 | 6/1987 | Japan | 73/24.02 |
| 2190998 | 12/1987 | United Kingdom | 73/24.02 |
| 22045 | 8/1995 | WIPO . | |

OTHER PUBLICATIONS

Patent Abstracts of Japan, vol. 011, No. 375 (P–644), Dec. 8, 1987 & JP 62 145143 A (Yokogawa Electric Corp), Jun. 29, 1987.

*Primary Examiner*—Daniel S. Larkin
*Attorney, Agent, or Firm*—Russell E. Baumann; Frederick J. Telecky, Jr.

[57] ABSTRACT

A gas sensor (10) is shown having alternately energized infrared radiation sources (14, 16) disposed in a gas chamber (12) at different distances from an infrared detector (18). Both radiation sources are filtered at the absorbing wavelength of a gas to be monitored with one radiation source located proximate to the detector serving as a "virtual reference". The differential absorption between the two radiation sources is used to determine the concentration of a gas being monitored. In a modified sensor (30) one radiation source is seated in a parabolic recess (34*a*) in a base plate (34) with the radiation focused on one angled end wall (32*d*) of a dished shaped cover member (32) and reflected over to a second angled end wall (32*e*) and into the detector with the radiation sources and the detector attached directly to a circuit board (24) mounting the sensor. The recessed cover with opposed angled end walls is also used with another embodiment in which the radiation sources are both located the same distance from the detector, are alternately energized and are filtered with sensing and reference filters, respectively. A modified embodiment (50) has a concave end wall (32*e*') vertically aligned with the detector and another embodiment (60) has an additional detector (18') along with a semi-reflective, semi-transmitting optical baffle (32*k*) for use with a gas having a higher absorption level. This embodiment also shows cover member (32") received directly on circuit board (24') with no intermediate base plate.

17 Claims, 6 Drawing Sheets

METHOD AND APPARATUS FOR INFRARED SENSING OF GAS

This application claims priority under 35 USC section 119 (e) (1) of provisional application No. 60/054,671 filed Aug. 4, 1997.

FIELD OF THE INVENTION

This application relates generally to gas sensors and more specifically to gas analyzers known as NDIR (nondispersive infrared analyzers).

BACKGROUND OF THE INVENTION

The ability of certain gases to absorb infrared radiation has been successfully utilized in developing instruments for gas sensing. In a simplified description, an infrared gas sensor comprises a narrow band infrared source (emitting radiation at the absorbing wavelength) and an infrared detector that are separated by a gas cell. The absorption is calculated from the infrared signals measured under zero gas (gas that does not have infrared absorption, e.g., nitrogen) $I(0)$, and under the gas of interest $I(G)$ using the relation, $$A = \frac{I(0) - I(G)}{I(0)}$$

However, this basic sensor configuration does not compensate for changes and deterioration of optical components with time and temperature. In practice, a reference channel is added to the sensor to correct for these potential problems. A reference channel is another band of infrared radiation that is not absorbed by the gas of interest. An ideal reference channel would use exactly the same optical path as the sensing channel and would not have any absorption by the gas of interest or by any other possible interfering gases. However, conventional sensors, in order be cost effective, do not satisfy the "ideal reference" conditions. For example, a sensor with one infrared source and two infrared detectors uses two different optical paths for the two channels that could change relative to one another over time and the two different detectors could age differently with time. These detectors could also have different temperature characteristics and need to be matched for optimum performance over temperature. The narrow band optical filters that are used to generate sensing and reference radiation are also sensitive to temperature. Therefore, the reference channel is not capable of correcting for any temperature drift caused by the pair of filters. In this example there are a total of four elements (2 detectors and 2 filters) that are sensitive to temperature and will contribute to temperature instability of the sensor. Another problem related to conventional gas sensing devices relates to the mechanical support structure needed to mount the infrared radiation source, detector, optical system and electronics in a reliable, durable and economical manner. In particular, the support structure for the optical components needs to be robust and mechanically stable. That is, it is important that there be no movement among the source, the optical assembly and the detector. Due to the relatively complex mechanical support required in conventional sensors for the radiation source and/or detector along with the light tube, such sensors are less robust than desired. For example, in a conventional light tube assembly which has a radiation source and a detector positioned at opposite ends of a tube, either one or both of the radiation source and the detector must be mounted remotely from the circuit board which contains the associated electronics and consequently additional wiring to the circuit board as well as mechanical supports are required. Further, such optical assemblies are not conducive for use with gases having different degrees of absorption. That is, the optical path between the IR light source and the detector is critical, particularly when gas concentrations with high IR absorption levels are of interest. Such gases require a sufficiently short optical path to provide suitable concentration resolution. On the other hand, when gas concentrations having low IR absorption levels are of interest, a relatively long optical path is required to provide suitable concentration resolution. It is difficult to adapt a tubular optical assembly for use with gases having different absorption characteristics.

SUMMARY OF THE INVENTION

It is an object of the present invention to provide a low cost gas sensor which is reliable, robust, mechanically stable and easily packaged, both mechanically and electrically. Another object of the invention is the provision of a method and apparatus for sensing having improved temperature stability. Another object is the provision of a gas sensor in which the selection of optical filters is simplified. Another object is the provision of an optical assembly which can easily be adapted for use with gas concentrations having different IR absorption levels. Yet another object of the invention is to overcome the above noted prior art limitations.

Briefly described, a method for sensing gas according to the invention comprises the steps of placing first and second infrared radiation sources at different distances from a radiation detector in a gas chamber, filtering the radiation received by the detector to a selected wavelength based on a gas to be sensed, electrically energizing the first and second radiation sensors in an alternating pattern, and comparing the electrical output signal of the radiation detector relating to the first and second radiation sources to determine the differential absorption of the selected wavelength as an indication of the concentration of the selected gas.

According to one preferred embodiment, the apparatus of the invention comprises a gas chamber having a radiation detector at one end of the chamber and a first infrared radiation source at the second end of the chamber focused toward the detector. A second infrared radiation source is placed in the chamber intermediate to the two opposite ends, preferably, relatively proximate to the detector with an appropriate filter disposed between the two sources and the detector. The chamber is shown mounted on a circuit board which also includes electronics for electrically energizing the first and second infrared radiation sources in an alternating pattern and for comparing the resulting electrical output signals of the detector relating to the respective sources to determine the differential absorption of the selected wavelength as an indication of the concentration of the gas within the chamber. In a modified embodiment, the gas chamber is formed by a generally flat base plate and a recessed shell-shaped cover member. The infrared radiation source is mounted in a parabolic recess formed in the base plate with the radiation focused onto an overlying, generally flat first end wall of the cover having an optically reflective surface and having an angle selected to reflect the radiation to the opposite, generally flat, second end wall also having an optically reflective surface. The radiation is in turn reflected downwardly to a filtered detector disposed in a well in the base plate aligned with the second end wall. A second infrared radiation source projects into the gas chamber through an aperture in the base plate, proximate to the detector. The cover and base plate are securely mounted to a printed circuit board through a spacer frame with the radiation sources and the detector directly connected mechanically and electrically to the circuit board.

According to another preferred embodiment, the recessed shell-shaped cover member, having oppositely disposed end walls sloped to serve as optical mirrors, is used with an optical system having first and second infrared radiation sources both having essentially the same optical path to the detector with each radiation source having a different, selected narrow band optical filter. In a modified embodiment the end wall aligned with the detector has a concave curved surface configuration. According to a feature of another modified embodiment, the cover is mounted, without any intermediate base member, directly on a circuit board on which the source, detector)and associated electronics are mounted. According to a feature of the invention, additional reflectors and detectors can be mounted within the chamber to provide different optical path lengths for use with gas concentrations having different absorption levels.

BRIEF DESCRIPTION OF THE DRAWINGS

Other objects, advantages and details of the novel and improved optical assembly for infrared gas sensors of the invention appear in the following detailed description of preferred embodiments of the invention, the detailed description referring to the drawings in which.

DETAILED DESCRIPTION OF THE PREFERRED EMBODIMENTS

Figure 1:
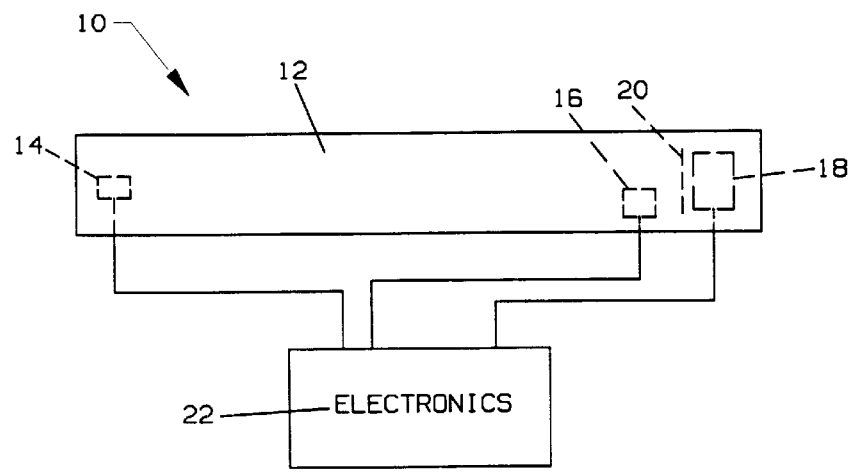
FIG. 1 is a schematic illustration of a gas sensor used in practicing the invention.

With respect to FIG. 1, a gas sensor 10 of the nondispersive infrared analyzer type made in accordance with the invention comprises a gas chamber 12 having an infrared radiation source 14 at a first end and a radiation detector 18 at a second, opposite end of the chamber. A second infrared radiation source 16 is disposed in chamber 12 intermediate to the first and second ends, that is, at a distance from the detector less than the distance between source 14 and detector 18. A narrow band optical filter 20 selected for a particular absorbing wavelength of a gas to be sensed is mounted between the infrared radiation sources and the detector. Electronics 22 are interconnected to the infrared radiation sources 14, 16 and detector 18 and are arranged to alternately energize the first and second source on a continuing basis and to compare the detector electrical output signal related to the energization signals to determine the differential absorption of the selected wavelength as an indication of the concentration of the gas being sensed within the gas chamber.

Figure 2:
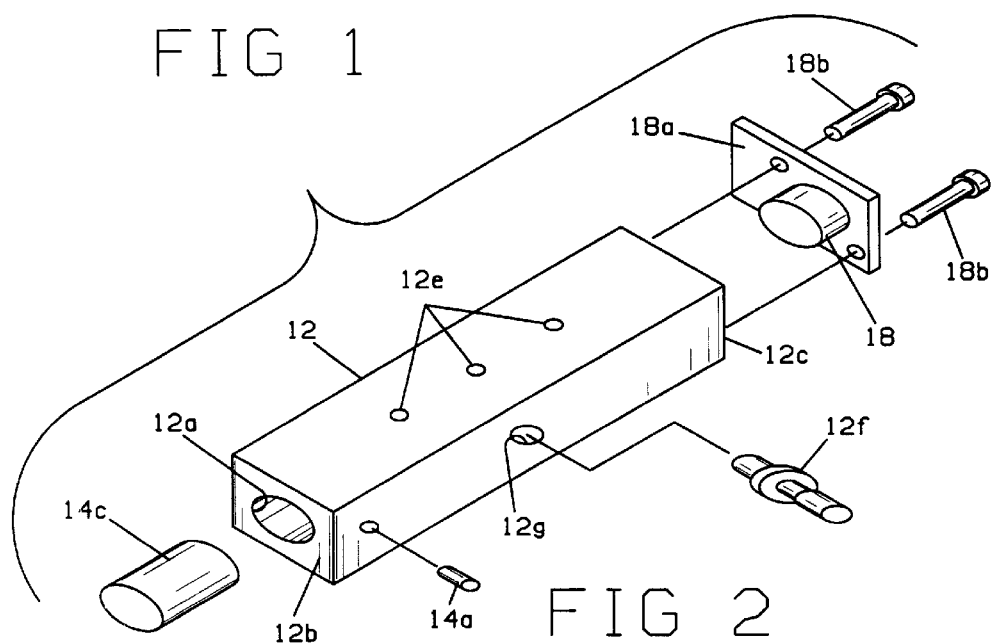
FIG. 2 is a blown-apart perspective of an optical assembly of a gas sensor made in accordance with one preferred embodiment of the invention.
Figure 3:
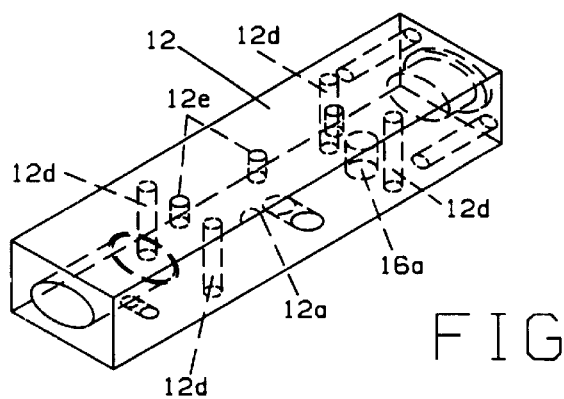
FIG. 3 is a schematic perspective of the optical tube portion of FIG. 2.
Figure 4:
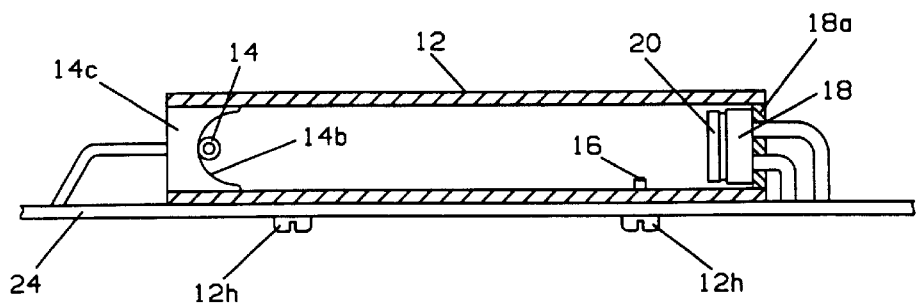
FIG. 4 is a cross sectional view of the FIG. 2 assembly, slightly simplified for purposes of illustration, mounted on a circuit board.
Figure 5A:
FIGS. 5a, 5b are graphs showing drive signals for alternately energizing first and second infrared radiation sources respectively.
Figure 5B:
Figure 6A:
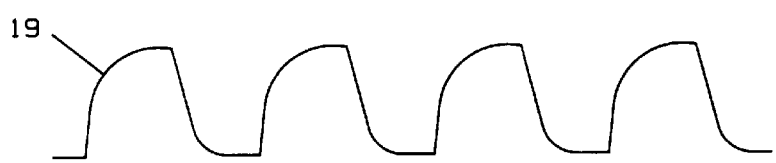
FIGS. 6a, 6b are graphs showing electrical output signals of a radiation detector in the presence of nitrogen and a selected gas to be detected, respectively.
Figure 6B:
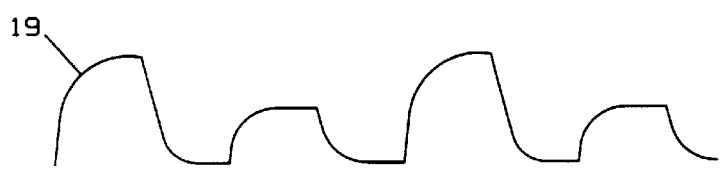

According to a preferred embodiment, as seen in FIGS. 2–4, gas chamber 12 is shown as an elongated parallelepiped of suitable material, such as aluminum, having a generally cylindrical bore 12a extending from a first end 12b to a second opposite end 12c. An infrared radiation source, comprised of a lamp 14 received in a focusing parabolic reflector seat 14b of housing 14c, is placed in bore 12a at the first end 12b and a radiation detector 18 is received in bore 12a at the second end 12c. Detector 18 includes a selected narrow band optical filter to filter out all radiation except for a given absorbing wavelength of a gas to be monitored. Housing 14c of radiation source 14 is locked in place by means of a set screw 14a and detector 18 is mounted on end plate 18a which, if desired, may comprise a circuit board and is in turn attached to chamber 12 by screws 18b. Chamber 12 is securely mounted to a suitable substrate, e.g., circuit board 24, by conventional fasteners 12h by means of threaded bores 12d indicated in FIG. 3. A plurality of ports 12e allow circulation of gas while a nozzle 12f, receivable in bore 12g, provides an alternative gas supply. As seen FIG. 4, infrared radiation source seat 14b is a parabolic optical reflective surface to focus the radiation directly toward radiation detector 18. A second infrared radiation source provided by lamp 16 is placed in chamber 12 at a location intermediate to its first and second ends, preferably proximate to detector 18. Due to the proximity of lamp 16 with detector 18, direct radiation emanating from lamp 16 is received by the detector and therefore need not be focused. Leads from lamp 16 are received through an aperture 16a in gas chamber 12 and can be soldered directly to circuit board 24. Suitable electronics 22 (FIG. 1) are mounted on circuit board 24 for alternately energizing first infrared radiation source 14 and second infrared radiation source 16 in a continuous pattern as shown by signals 15, 17 and FIGS. 5a, 5b, respectively, and to compare the electrical output signal 19 of radiation detector 18 related to the radiation of sources 14 and 16 to determine the differential absorption of the selected wave length as an indication of the concentration of the selected gas (FIG. 6b).

Since radiation source 16 is closer than source 14 to detector 18, the radiation from source 16 will travel a shorter optical path to the detector than the radiation from source 14. Infrared radiation from both sources 14 and 16 are filtered at the absorbing wavelength before entering detector 18 and each is absorbed by the gas being monitored. Since the radiation from source 16 travels a shorter path through the gas, less radiation will be absorbed than that from source 14, resulting in a differential absorption as seen in FIG. 6b and this differential absorption is used to determine the gas concentration. The output detector signal related to source 16 serves as a virtual reference to the system operating at the absorption wavelength. If desired, the comparison of the output signal relative to the two sources may be facilitated by adjusting the power level of drive signal 17 of source 16 relative to the power level of signal 15 of source 14 so that the strength of the output signal 19 of detector 18 relative to the two sources is made nearly equal in the presence of a non-absorbing gas such as nitrogen, as shown in FIG. 6a.

Among the advantages provided by this embodiment may be noted that only one optical filter is employed so that the constraints which normally apply in selecting a reference wavelength are eliminated. The provision of a "virtual reference" channel which is also at the absorbing wavelength results in improved temperature independent performance. Additionally, these advantages are realized utilizing an inexpensive and simple apparatus for the sensor. Although this embodiment does not compensate or correct for changes which may take place regarding the optical properties of the assembly, such as those caused by dust and oxidation of any reflective surfaces, this can easily be minimized by using dust filters on the gas inlet ports and by using pre-oxidized reflective optics. Although radiation source 14 is shown focused directly to detector 18, it is within the purview of the invention to employ a multiple reflection configuration, such as that provided by a conventional light tube to enhance the signal from source 14.

As noted above, mechanical stability is a critical requirement for a reliable, accurate gas sensor. The above described embodiment can be mounted directly and securely on a circuit board 24 and radiation source 16 can be soldered directly to the circuit board. According to a modified embodiment shown in FIGS. 7–12, radiation source 14 and detector 18 can also be directly connected, as by soldering, to circuit board 24. Gas sensor 30 of the modified embodiment comprises a recessed shell configured cover member 32, a generally planar base plate 34, and spacer frame 36. Gas sensor 30 is shown conveniently mounted on circuit board 24 using conventional fasteners 38. Radiation sources 14, 16 and detector 18 are mounted directly on circuit board 24 and are received through seating apertures in base plate 34 to be discussed.

Figure 9:
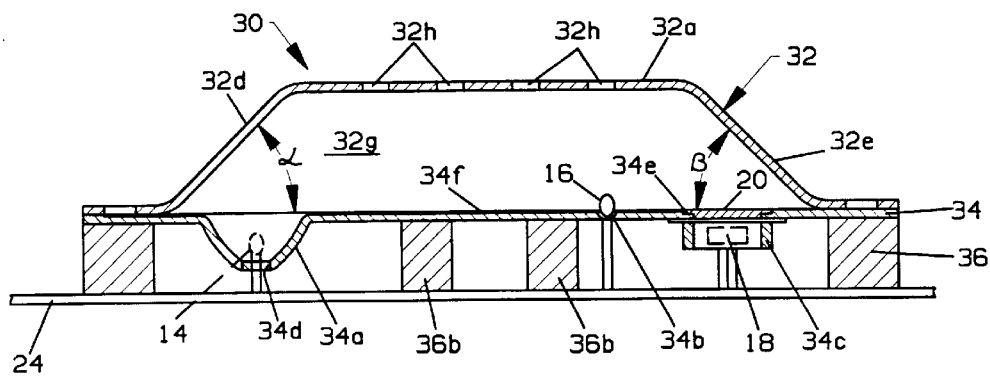
FIG. 9 is a cross sectional view taken on line 9—9 of FIG. 8.
Figure 10:
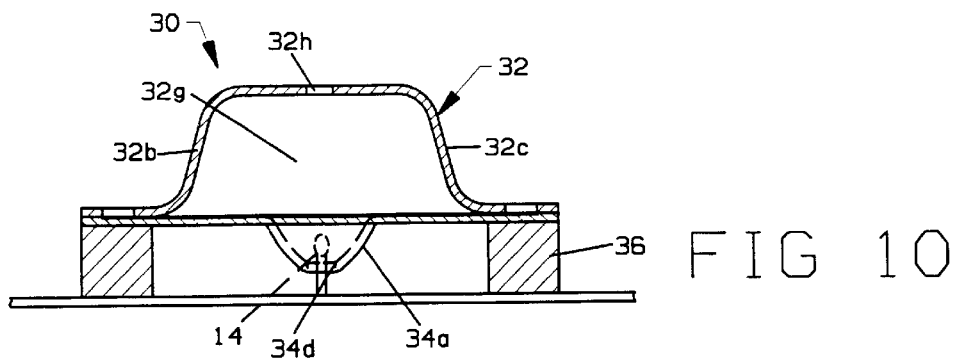
FIG. 10 is a cross sectional view taken on line 10—10 of FIG. 8.
Figure 11:
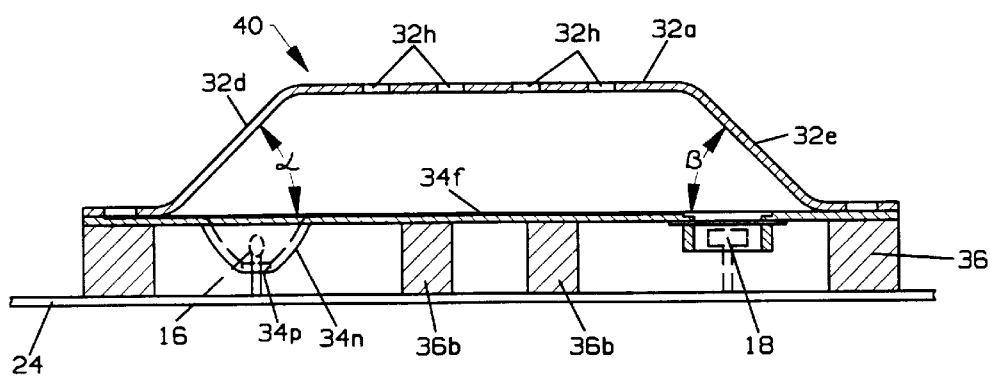
FIGS. 11, 12 are cross sectional views similar to FIGS. 9 and 10, respectively, of another embodiment of the invention.
Figure 12:
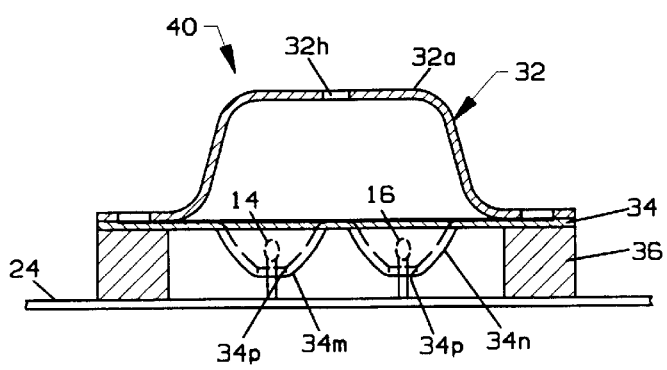
Figure 13:
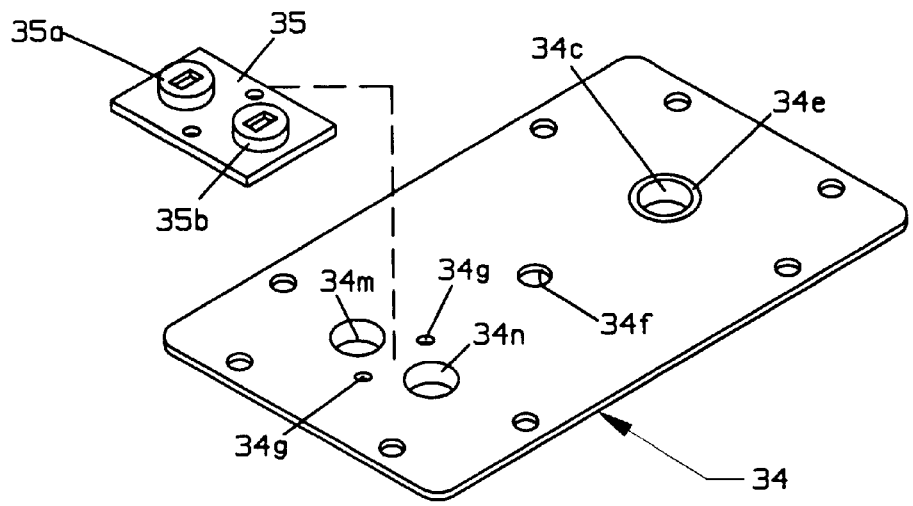
FIG. 13 is a reduced scale perspective view of a base plate used in the FIGS. 11, 12 assembly.
Figure 14:
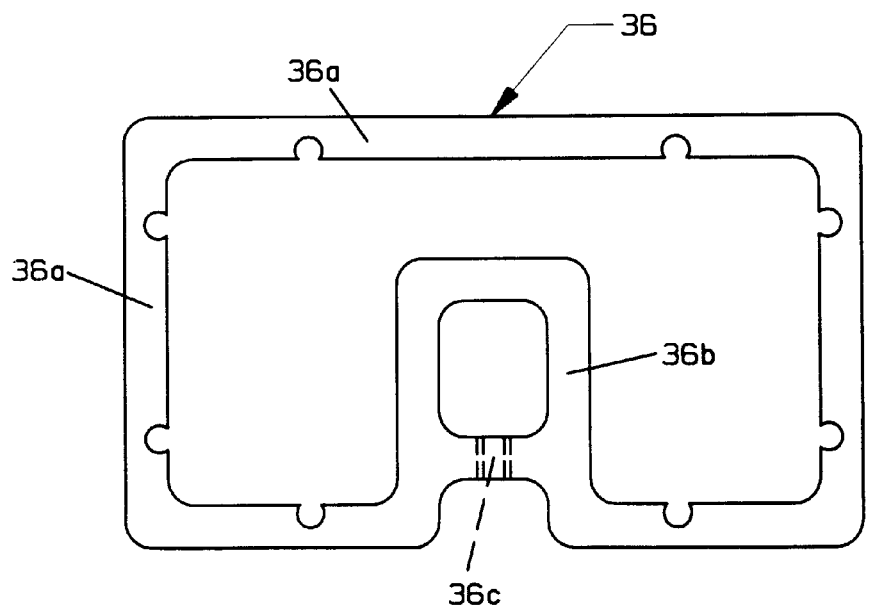
FIG. 14 is a reduced scale top plan view of a base plate frame used in the FIGS. 11, 12 assembly.

Cover member 32, composed of suitable material having an optically reflective surface for the optical wavelength of concern, such as aluminum for infrared radiation, comprises a top wall 32a with opposed sidewalls 32b, 32c and opposed end walls 32d, 32e extending to a flat marginal flange 32f forming a recess 32g which serves as a gas chamber. Cover member 32 has apertures 32h therethrough and can be formed by conventional stamping procedures. Flange 32f is received on base plate 34 enclosing the chamber. Base plate 34, see FIG. 9, is provided with radiation source mounting seats 34a, 34b and a detector seat 34c. Radiation source seat 34a is, preferably, formed with a parabolic surface recessed below the plane of plate 34 to function as a parabolic reflector and has a lamp receiving aperture 34d for reception of lamp 14. Radiation source seat 34b is in the form of a lamp receiving aperture for lamp 16. End walls 32d and 32e are generally flat walls forming a selected angle, alpha, beta, respectively, with the plane in which base plate 34 lies. Sidewalls 32b, 32c may be formed having any convenient angle suitable for stamping purposes. In the embodiment shown, angles alpha and beta are, preferably, approximately 45°. Radiation source seat 34a is vertically aligned with flat wall 32d to form a specular reflector of IR radiation from radiation source 14, focused by the parabolic surface, to end wall 32e which then reflects the radiation to detector 18 disposed in detector seat 34c. The optical filter may be integrally mounted on detector 18 as in the FIGS. 2–4 embodiment or filter 20 could be mounted in annular recess 34e of detector seat 34c as shown in FIG. 9. Preferably, a spacer frame 36, also shown in FIG. 14, is used to facilitate mounting of the optical assembly to circuit board 24 providing space for recess seats 34a, 34c. An internal enclosure shaped portion 36b may be provided, if desired, in communication with bore 34f of base plate 34 providing an optional gas inlet through a coupling receiving bore 36c, such as nozzle 12f of FIG. 2. Operation of the gas sensor is the same of that described above relating to FIGS. 2–6.

The co-planar configuration of the optical assembly of FIGS. 7–10 can also be used in sensor designs other than the previously described "virtual reference" type. One such example, a two source, one detector embodiment, is shown in FIGS. 11–14. Gas sensor 40 in this embodiment utilizes the same cover 32 and frame 36 of the FIGS. 7–10 embodiment; however, base plate 34 is provided with first and second recessed, parabolic IR radiation source seats 34m, 34n vertically aligned with end wall 32d and positioned so that both have essentially equal optical paths to detector 18. Radiation seats 34m, 34n are both provided with a lamp receiving aperture 34p for reception of first and second radiation sources 14, 16. Apertures 34g in base plate 34 are provided for a filter assembly 35 (FIG. 13) for placement of sensing filter 35a and a reference filter 35b respectively, over seats 34m, 34n. As shown in FIG. 14, spacing frame 36 provides an enclosed peripheral support 36a of any suitable material having a height selected to provide vertical clearance for radiation source seats 34m, 34n. An internal enclosure shaped portion 36b may be provided, if desired, in communication with bore 34f of base plate 34 providing an optional gas inlet through a coupling receiving bore 36c, such as nozzle 12f of FIG. 2.

In operation of gas sensor 40, radiation sources 14, 16 are energized alternately and the radiation from the first and second radiation sources 14, 16 are filtered by the respective sensing and reference filters with the collimated radiation directed to detector 18 using the two 45° end wall surfaces 32d, 32e.

Figure 7:
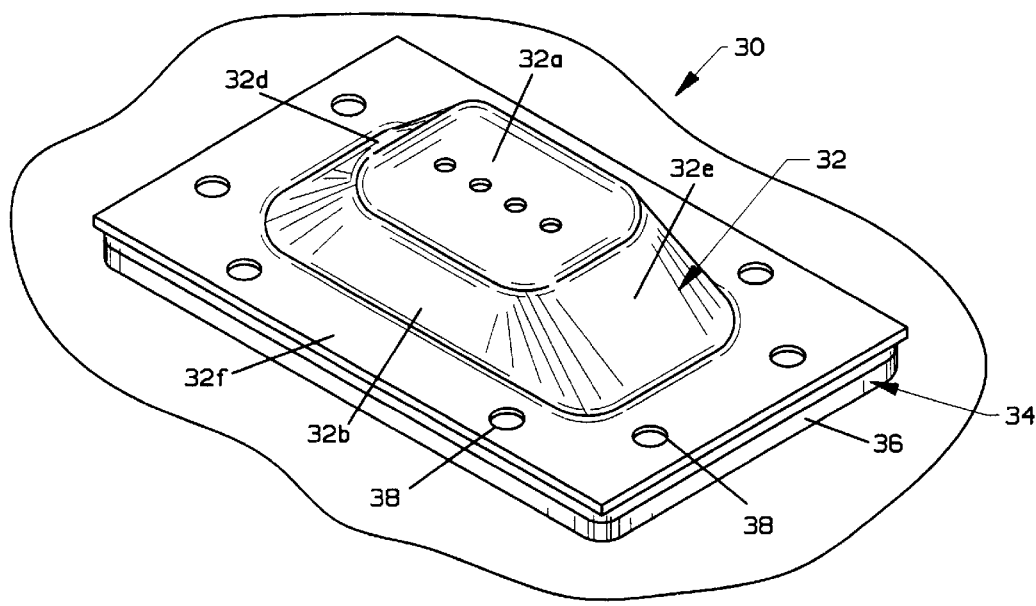
FIG. 7 is a perspective view of an optical assembly made in accordance with a modified embodiment of the invention.
Figure 8:
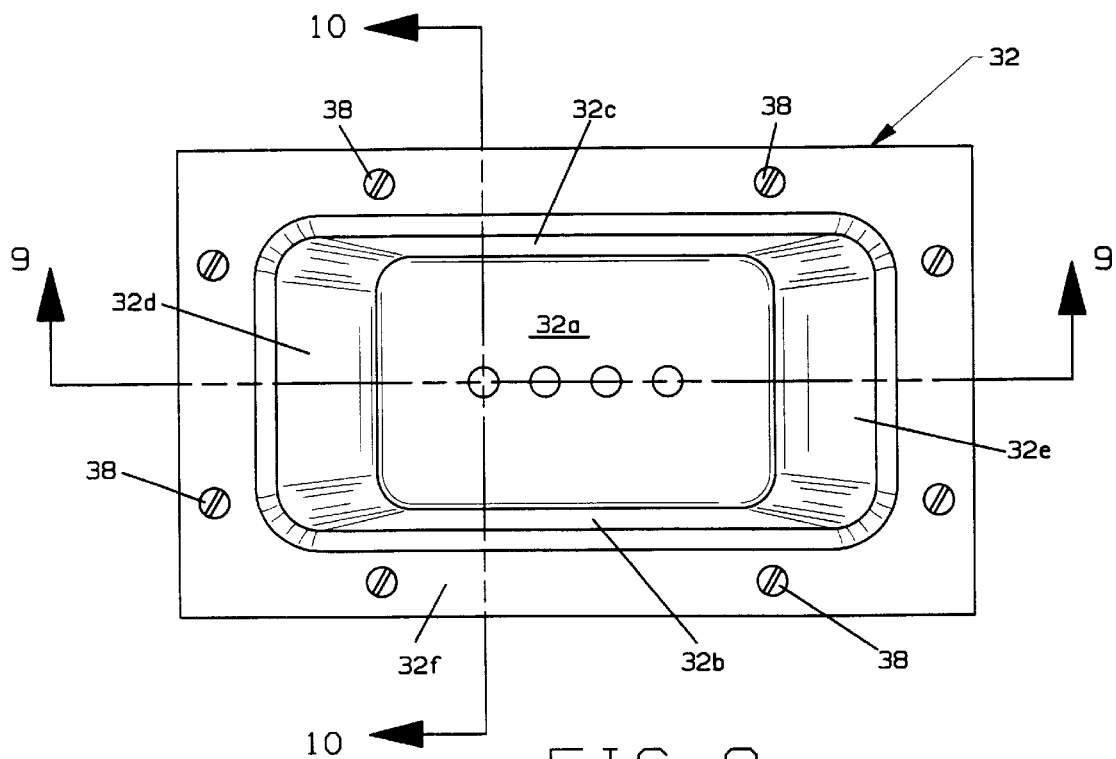
FIG. 8 is a top plan view of the FIG. 7 optical assembly.

As mentioned above, light sources 14, 16 and detector 18 are, preferably, directly attached, as by soldering or the like, to circuit board 24 and then base plate 34, with base frame 36, is placed on circuit board 24 with the light sources and detector received in their respective seats. Cover member 32 is then placed on base plate 34 and the optical assembly is securely fastened using fasteners 38 (FIGS. 7, 8).

It will be understood that, in like manner, the co-planar configuration can also be used with a one source, two detector arrangement.

Figure 15:
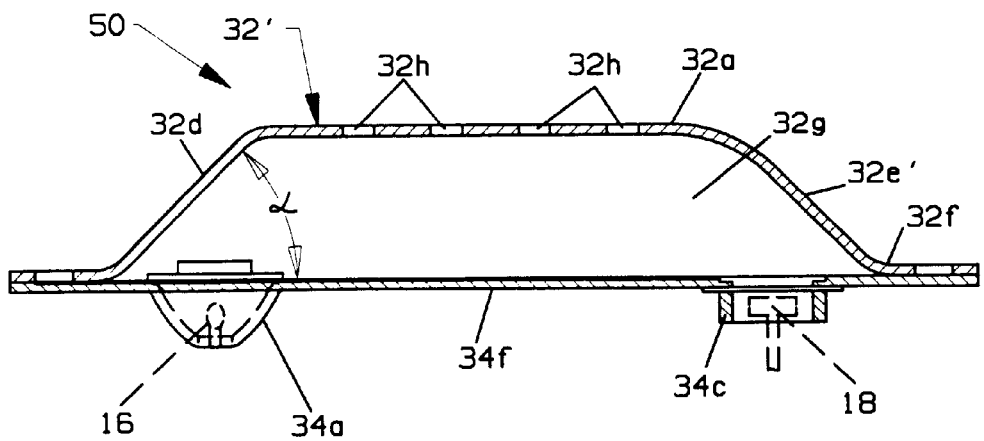
FIG. 15 is a cross sectional view of a modification of the FIGS. 11, 12 embodiment.

FIG. 15 shows a modified optical assembly 50 in which end wall 32e' is formed with a concave surface, such as a spherical surface, to further focus the reflected light to the detector. In other respects, the assembly is the same as in the FIGS. 11–14 embodiment so that the description need not be repeated.

Figure 16:
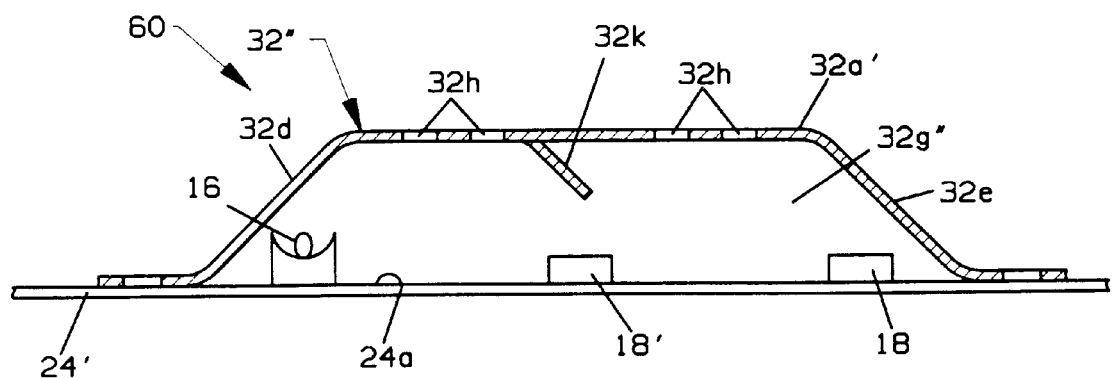
FIG. 16 is a cross sectional view of another modification of the FIGS. 11, 12 embodiment.

With respect to FIG. 16, another modified optical assembly 60 is shown in which cover member 32" is mounted directly on circuit board 24' on a portion 24a. Cover member 32" has a top wall portion 32a' and end walls 32d, 32e, forming a selected angle, e.g., 45°, with the plane of the circuit board in the same manner as in the FIGS. 11–14 embodiment. Focused radiation lamp sources 14, 16, having appropriate filters, are connected to circuit board 24', and are vertically aligned with end wall 32d while detector 18, also directly connected to circuit board 24', is vertically aligned with end wall 32e. A second detector 18' may also be mounted in chamber 32g" or use with a gas having a relatively higher absorption and may be vertically aligned with a semi-reflecting and semi-transmitting optical baffle 32k. If desired, additional optical baffles 32k (not shown) may be provided on wall 32a' to provide different effective optical path lengths.

In view of the above, it will be seen that gas sensors made in accordance with certain embodiments of the invention provide a "virtual reference" channel which is also at the absorbing wavelength resulting in improved temperature independent performance using a minimal number of components making it extremely cost effective and eliminating the need for locating an infrared region for the reference channel. Sensors made in accordance with the invention provide a simple, accurate, robust and extremely stable structure for precisely positioning and mounting the optical components. The electrical and mechanical mount is also greatly facilitated.

It should be noted that although preferred embodiments of the invention have been described by way of illustrating the invention, the invention includes all modifications and equivalents of the disclosed embodiments falling within the scope of the appended claims.

What is claimed:

1. A method for indicating the concentration of a selected gas to be monitored comprising the steps of:

forming a gas chamber, placing an infrared radiation detector having an electrical output signal within the chamber, placing a first infrared radiation source in the chamber at a first distance from the detector, placing a second infrared radiation source in the chamber at a second distance from the detector, the first distance being greater than the second distance, placing a selected narrow band optical filter between infrared radiation sources and the detector, allowing the introduction of a selected atmosphere into the gas chamber, alternately energizing the first and second infrared radiation sources and comparing the detector electrical output signal related to the radiation of the first and second infrared sources to determine the differential absorption of the selected wavelength as an indication of the concentration of a selected gas to be monitored in the atmosphere introduced into the gas chamber.

2. A method according to claim 1 further comprising the step of focusing the radiation from the first infrared source toward the detector.

3. A method according to claim 1 further comprising the step of using generally flat optical mirrors to reflect the radiation from the first infrared source to the detector.

4. A method according to claim 1 in which the levels of energization of the first and second infrared radiation sources are calibrated prior to use with a selected gas comprising the steps, prior to the introduction of the selected atmosphere into the chamber, of introducing a gas which has no infrared absorption into the gas chamber and then adjusting the level of energization of the second infrared radiation relative to the level of energization of the first infrared radiation source until the detector output signals related to the first and second infrared radiation sources are approximately equal to one another.

5. Gas sensor apparatus for indicating the concentration of a selected gas comprising:

a gas chamber, a port for introducing a selected atmosphere into the chamber, an infrared radiation detector mounted in the chamber having an electrical output signal, a first infrared radiation source mounted in the chamber at a first distance from the detector, a second infrared radiation source mounted in the chamber at a second distance from the detector less than the first distance, a narrow band optical filter disposed between the detector and the first and second infrared radiation sources, and means to alternately energize the first and second infrared radiation sources and to compare the electrical output signal of the detector related to the first and second infrared radiation sources.

6. Gas sensor apparatus according to claim 5 in which the gas chamber comprises a dish-shaped cover member having first and second end walls disposed at respective, selected angles relative to a reference plane and the first infrared radiation source includes a focusing surface focusing the radiation from the first infrared radiation source toward the first end wall, the angle of the first end wall selected so that the radiation from the first infrared radiation source is reflected to the second end wall and the angle of the second end wall selected so that the reflected radiation from the first end wall is reflected toward the detector.

7. Gas sensor apparatus according to claim 6 in which the selected angles of the first and second end walls relative to the reference plane are both 45 degrees.

8. Gas sensor apparatus according to claim 5 further including a circuit board and the first and second infrared radiation sources include lamps having leads which are directly soldered to the circuit board.

9. Gas sensor apparatus according to claim 8 in which the radiation detector has leads which are directly soldered to the circuit board.

10. Gas sensor apparatus for indicating the concentration of a gas comprising:

a generally planar first surface and a second generally dish-shaped cover member received on the first surface forming a gas chamber having optically reflecting surface portions, the cover member having a top wall portion and first and second opposed end walls;

a gas inlet to the gas chamber;

a circuit board; and radiation source means having at least one radiation source element disposed adjacent the first end wall and a radiation sensing detector means having at least one radiation sensing detection element disposed adjacent the second end wall at a selected distance from the at least one radiation source element wherein at least one of said radiation source means and said radiation sensing detector means has more than one of the group consisting of radiation source element and radiation sensing detector element;

said first surface having a parabolic recess formed therein with an aperture for receiving said radiation source means which includes a lamp having electrical leads mounted directly to the circuit board and a well formed therein for receiving said radiation sensing detector means with electrical leads mounted directly to the circuit board.

11. Gas sensor apparatus according to claim 10 in which the end walls are generally planar.

12. Gas sensor according to claim 10 in which the second end wall has a curved surface in the form of a concave configuration facing the first surface.

13. Gas sensor apparatus according to claim 10 in which the first and second end walls are generally planar, each end wall being disposed at an angle of approximately 45° with the first surface, the parabolic shaped recess is vertically aligned with the first end wall and the well is vertically aligned with the second end wall.

14. Gas sensor apparatus according to claim 10 further comprising a second radiation sensing element disposed in the gas chamber at a second distance from the radiation source means less than the selected distance and an optically semi-reflective and semi-transmitting baffle extends downwardly from the top wall portion aligned with the second radiation sensing detector.

15. Gas sensor apparatus for indicating the concentration of a gas comprising:

a generally planar first surface and a second generally dish-shaped cover member received on the first surface forming a gas chamber having optically reflecting surface portions, the cover member having a top wall portion and first and second opposed end walls;

a gas inlet to the gas chamber;

a circuit board, the first surface comprising a top surface of the circuit board; and radiation source means having at least one radiation source disposed adjacent the first end wall and a radiation sensing detector means having at least one radiation sensing detector element disposed adjacent the second end wall at a selected distance from the at least one radiation source element wherein at least one of said radiations source means and said radiation sensing detector means has more than one of the group consisting of radiation source element and radiation sensing detector element.

16. Gas sensor apparatus for indicating the concentration of a gas comprising:

a generally planar first surface and a second generally dish-shaped cover member received on the first surface forming a gas chamber having optically reflecting surface portions, the cover member having a top wall portion and first and second opposed end walls;

a gas inlet to the gas chamber;

a circuit board and a base plate mounted on the circuit board, the first surface comprising a top surface of the base plate; and radiation source means having at least one radiation source element disposed adjacent the first end wall and a radiation sensing detector means having at least one radiation sensing detector element disposed adjacent the second end wall at a selected distance from the at least one radiation source element wherein at least one of said radiation source means and said radiation sensing detector means has more than one of the group consisting of radiation source element and radiation sensing detector element.

17. Gas sensor apparatus according to claim 16 further comprising a parabolic shaped recess formed in the base plate for reception of the radiation source means, a well formed in the base plate for reception of the radiation sensing detector, and a base frame disposed between the base plate and the circuit board to provide vertical spacing for the parabolic shaped recess and the well.

* * * * *